US012599573B2

(12) United States Patent
Shan et al.

(10) Patent No.: US 12,599,573 B2
(45) Date of Patent: Apr. 14, 2026

(54) COMPOSITIONS AND USES THEREOF IN TREATING CANCERS

(71) Applicant: NATIONAL CHENG KUNG UNIVERSITY, Tainan City (TW)

(72) Inventors: Yan-Shen Shan, Tainan City (TW); Chang-Jung Chen, Tainan City (TW); Hao-Chen Wang, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 409 days.

(21) Appl. No.: 18/185,630

(22) Filed: Mar. 17, 2023

(65) Prior Publication Data

US 2024/0307318 A1 Sep. 19, 2024

Related U.S. Application Data

(60) Provisional application No. 63/320,714, filed on Mar. 17, 2022.

(51) Int. Cl.
*A61K 9/51* (2006.01)
*A61K 31/713* (2006.01)
*A61P 35/00* (2006.01)

(52) U.S. Cl.
CPC .......... *A61K 9/5123* (2013.01); *A61K 31/713* (2013.01); *A61P 35/00* (2018.01)

(58) Field of Classification Search
None
See application file for complete search history.

(56) References Cited

U.S. PATENT DOCUMENTS

2011/0111044 A1* 5/2011 Zhao ....................... A61P 35/04
977/773

* cited by examiner

*Primary Examiner* — Celeste A Roney
(74) *Attorney, Agent, or Firm* — NZ Carr Law Office

(57) ABSTRACT

Disclosed herein is a composition comprising a lipid nanoparticle and a double-stranded oligodeoxynucleotide (dsODN) encapsulated in the lipid nanoparticle. According to the embodiments of the present disclosure, the dsODN comprises two strands complementary to each other, in which the first strand comprises the nucleotide sequence of SEQ ID NO: 1. Also disclosed herein are methods of treating cancers by using the present composition.

4 Claims, 5 Drawing Sheets

Specification includes a Sequence Listing.

(A)

(B)

(C)

(D)

(A)

(B)

(A)

(B)

COMPOSITIONS AND USES THEREOF IN TREATING CANCERS

CROSS-REFERENCE TO RELATED APPLICATIONS

This application relates to and claims the benefit of U.S. Provisional Application No. 63/320,714, filed Mar. 17, 2022; the content of the application is incorporated herein by reference in its entirety.

SEQUENCE LISTING XML

The present application is being filed along with a Sequence Listing XML in electronic format. The Sequence Listing XML is provided as a XML file entitled AJ23003N_Sequence_Listing, created Mar. 3, 2023, which is 7 Kb in size. The information in the electronic format of the Sequence Listing XML is incorporated herein by reference in its entirety.

BACKGROUND OF THE INVENTION

1. Field of the Invention

The present disclosure in general relates to the field of cancer treatment. More particularly, the present disclosure relates to double-stranded oligodeoxynucleotides (dsODNs), and methods of treating cancers by using the dsODNs.

2. Description of Related Art

Cancer is a disease characterized by the development of abnormal cells that divide uncontrollably and may infiltrate and destroy normal tissues. As a leading cause of death worldwide, cancer accounts for nearly 10 million deaths in 2020. The most common causes of cancer death in 2020 includes lung, colon and rectum, liver, stomach, and breast cancers. Cancer signs and symptoms usually vary with the types of cancers and the affected body part; for example, lung cancer symptoms include coughing, chest pain, shortness of breath, wheezing, fatigue and weigh loss; the symptoms associated with colon and rectum cancer include a change in bowel habits (e.g., diarrhea, constipation and narrowing of the stool), bleeding, cramping, abdominal pain, fatigue and weight loss; and the main symptoms of liver cancer include the loss of appetite, nausea, vomiting, abdominal swelling, jaundice, fatigue, weight loss, and white and chalky stools.

Macrophages are highly specialized cells that play diverse roles in the development, tissue homeostasis, pathogen infection, tissue injury and tissue repair. In addition, macrophages also form a major component of tumor microenvironment (TME). The tumor-associated macrophages (TAMs, i.e., the macrophages present in the TME) could be classified into two phenotypes, classical-activated macrophages (also known as M1 macrophages) and alternative-activated macrophages (also known as M2 macrophages). In general, M1 macrophages foster inflammation response against tumor cells, while M2 macrophages exhibit an immune suppressive activity that supports tumor angiogenesis and promotes tumor progression. These two types of macrophages are distinct in their markers, metabolic characteristics, and gene expression profiles; for example, M1 macrophages secrete pro-inflammatory molecules, including interleukin (IL)-12, tumor necrosis factor (TNF)-α, C-C motif ligand (CCL)-2, C-X-C motif ligand (CXCL)-10 and interferon (IFN)-γ; while M2 macrophages secrete immunosuppressive molecules, including IL-4, IL-10 and transforming growth factor (TGF)-β. Further, M2 macrophages are known to promote tumor vascularization via producing pro-angiogenic factors, such as vascular endothelial growth factor (VEGF)-A and VEGF-C. Based on the immunosuppressive activity in the TME, M2 macrophages may serve as a target for immunotherapy drug development.

There are different types of cancer treatment, including surgery (an operation removing cancer from patients), radiation therapy (i.e., killing cancer cells by high-powered energy beams, such as X-rays or protons), chemotherapy (i.e., killing cancer cells by cytotoxic drugs), and hormone therapy (i.e., reducing the level of hormones in patients so as to inhibit the growth of hormone-related cancers, for example, breast and prostate cancers). However, none of these treatments provides a satisfactory result due to the limitation of various side-effects, such as bleeding, the risk of infection, anemia, thrombocytopenia, lymphedema, nausea, vomiting, diarrhea, edema, constipation, neuropathy, and memory or concentration problems. In addition, In view of the foregoing, there is a continuing interest in developing a novel method for treating cancers.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of the present disclosure is directed to a double-stranded oligodeoxynucleotide (dsODN) comprising a first strand and a second strand complementary to the first strand. According to embodiments of the present disclosure, the first strand comprises the nucleotide sequence of SEQ ID NO: 1 ("TTCAAGTGAT").

According to some exemplary embodiments, the first strand comprises a nucleotide sequence at least 85% identical to SEQ ID NO: 3 ("CTGACTCCCAGGTTCAAGT-GATTCTCCT"); preferably, at least 90% identical to SEQ ID NO: 3; more preferably, at least 95% identical to SEQ ID NO: 3. In some working examples, the first strand comprises a nucleotide sequence 100% identical to SEQ ID NO: 3.

Also disclosed herein is a composition comprising the present dsODN. According to some embodiments, the composition comprises the dsODN of the present disclosure, and a lipid nanoparticle (LNP), in which the LNP has a hydrophilic core and an outer lipid bilayer, and the dsODN is encapsulated within the hydrophilic core of the LNP.

Optionally, the composition further comprises an anti-cancer agent encapsulated in the hydrophilic core of the LNP.

The present disclosure also provides a method of treating a cancer by using the dsODN or composition of the present disclosure. The method comprises administering to the subject an effective amount of the present dsODN or composition.

Examples of cancer treatable with the present method include, but are not limited to, gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, and head and neck squamous cell carcinoma.

In general, the subject is a mammal; preferably, a human.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings.

DETAILED DESCRIPTION OF THE INVENTION

Figure 1:
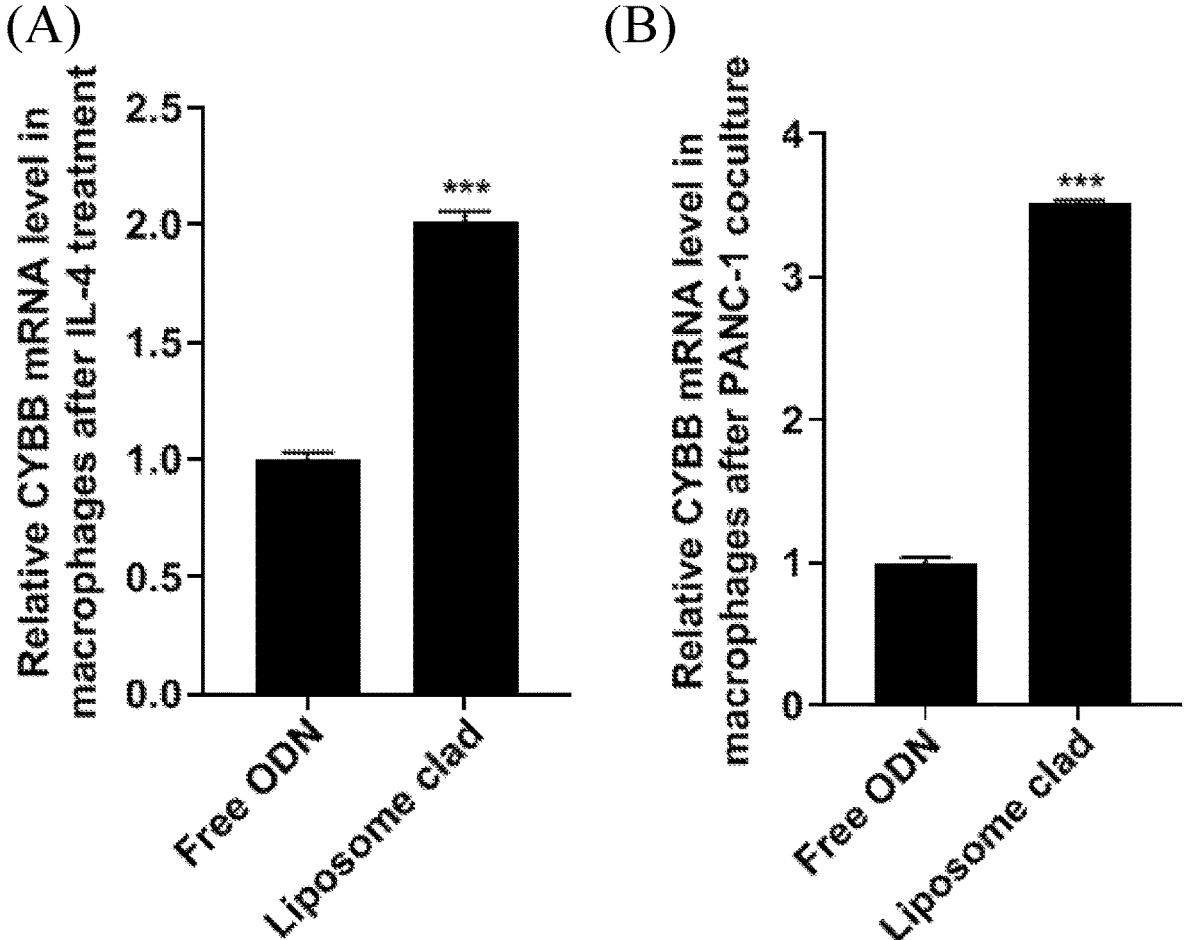
FIG. 1 depicts the mRNA level of CYBB gene in macrophages according to Example 3 of the present disclosure, in which the U937 cells were treated with CYBB decoy ODN (free-ODN) or liposome-clad decoy ODN (liposome clad), followed by incubating in the medium containing IL-4 (Panel (A)) or co-incubating with PANC-1 cells (Panel (B)). ***, $p<0.001$.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "deoxynucleotide" refers to a nucleotide or polynucleotide lacking a hydroxyl group (OH group) at the 2 position and/or 3 position (2' carbon and/or 3' carbon) of a sugar moiety; instead, the nucleotide or polynucleotide has a hydrogen (H) bonded to the 2' carbon and/or 3' carbon of the sugar moiety. According to some embodiments of the present disclosure, the term "oligodeoxynucleotide" (ODN) refers to a polynucleotide having less than 50 nucleotides (i.e., an oligonucleotide), in which each nucleotide comprises a sugar moiety having a hydrogen (H) bonded to its 2 position.

"Percentage (%) sequence identity" is defined as the percentage of nucleotides in a candidate sequence that are identical with the nucleotides in the specific nucleotide sequence, after aligning the sequences and introducing gaps, if necessary, to achieve the maximum percent sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two nucleotide sequences was carried out by computer program BLASTN (nucleotide-nucleotide BLAST) provided online by Nation Center for Biotechnology Information (NCBI). The percentage sequence identity of a given nucleotide sequence A to a given nucleotide sequence B (which can alternatively be phrased as a given nucleotide sequence A that has a certain % nucleotide sequence identity to a given nucleotide sequence B) is calculated by the formula as follows:

$$\frac{X}{Y} \times 100$$

where X is the number of nucleotides scored as identical matches by the sequence alignment program BLAST in that program's alignment of A and B, and where Y is the total number of nucleotides in A or B, whichever is shorter.

The phrase "pharmaceutically acceptable" refers to molecular entities and compositions that are "generally regarded as safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "administered", "administering" or "administration" are used interchangeably herein to refer a mode of delivery, including, without limitation, intratumorally, intravenously, intraarterially, intraperitoneally, intramuscularly or subcutaneously delivering an agent (e.g., the dsODN or composition) of the present invention.

As used herein, the term "treat," "treating" and "treatment" are interchangeable, and encompasses partially or completely preventing, ameliorating, mitigating and/or managing a symptom, a secondary disorder or a condition associated with cancer. The term "treating" as used herein refers to application or administration of the composition of the present disclosure to a subject, who has a symptom, a secondary disorder or a condition associated with cancer, with the purpose to partially or completely alleviate, ameliorate, relieve, delay onset of, inhibit progression of, reduce severity of, and/or reduce incidence of one or more symptoms, secondary disorders or features associated with cancer. Symptoms, secondary disorders, and/or conditions associated with cancer include, but are not limited to, fatigue, pain, bleeding, lump, a change in bowel or bladder habit, coughing or trouble breathing, hoarseness, fever, loss of appetite and weigh loss. Treatment may be administered to a subject who exhibits only early signs of such symptoms, disorder, and/or condition for the purpose of decreasing the risk of developing the symptoms, secondary disorders, and/or conditions associated with cancer. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Persons having ordinary skills could calculate the human equivalent dose (HED) for the medicament (such as the present dsODN or composition) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with the dsODN, composition, and/or method of the present invention. The term "subject" is intended to refer to both the male and female gender unless one gender is specifically indicated.

II. Description of the Invention

The present disclosure is based, at least in part, on the discovery that a double-stranded oligodeoxynucleotide (dsODN) comprising specific nucleotide sequence may serve as a decoy ODN that tilts the balance toward macrophage M1 polarization, i.e., augmenting M1 macrophage differentiation and diminishing M2 macrophage differentiation, via inhibiting the binding of signal transducer and activator of transcription 6 (STAT6) and histone deacetylase 2 (HDAC2) to CYBB promoter. Accordingly, the present disclosure aims at providing a method of treating cancers by using the dsODN or a composition comprising the dsODN.

The first aspect of the present disclosure is thus directed to a dsODN, which comprises two complementary strands of nucleic acids. According to embodiments of the present disclosure, the first strand (or the sense strand) comprises a core sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of "TTCAAGTGAT" (SEQ ID NO: 1, from 5'-end to 3'-end), and the second strand (or the antisense strand) comprises a complementary core sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99% or 100%) identical to nucleotide sequence of "ATCACTTGAA" (SEQ ID NO: 2, from 5'-end to 3'-end). Preferably, the first and second strands of the present dsODN respectively comprise the nucleotide sequences at least 90% identical to SEQ ID NOs: 1 and 2. In some preferred embodiments, the first strand of the present dsODN comprises the nucleotide sequence 100% identical to SEQ ID NO: 1, and the second strand of the present dsODN comprises the nucleotide sequence 100% identical to SEQ ID NO: 2.

Optionally, in addition to the core sequences, each of the first and second strands may further comprise additional nucleotides disposed at the 5'-end and/or 3'-end of the core sequences. According to certain preferred embodiments, the first strand further comprises 12 and 6 nucleotides respectively disposed at and connected to the 5'-end and 3'-end of the core sequence (SEQ ID NO: 1), and the second strand further comprises 6 and 12 nucleotides respectively disposed at and connected to the 5'-end and 3' end of the core sequence (SEQ ID NO: 2). In these embodiments, the first and second strands respectively comprise the nucleotide sequence of "CTGACTCCCAGGTTCAAGTGATTCTCCT" (SEQ ID NO: 3, from 5'-end to 3'-end; the core sequence is in italic font) and "AGGAGAATCACTTGAACCTGGGAGTCAG" (SEQ ID NO: 4, from 5'-end to 3'-end; the core sequence is in italic font).

As could be appreciated, one or more nucleotides of the first and/or second strand(s), especially the nucleotides disposed at the 5'-end or 3'-end of the core sequence, may vary without affecting the stability and binding activity of the present dsODN. According to some embodiments, the first strand of the present dsODN comprises a nucleotide sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99% or 100%) identical to SEQ ID NO: 3, and/or the second strand of the present dsODN comprises a nucleotide sequence at least 80% (e.g, 80%, 81%, 82%, 83%, 84%, 85%, 86%, 87%, 88%, 89%, 90%, 91%, 92%, 93%, 94%, 95%, 96%, 97%, 98%, 99% or 100%) identical to SEQ ID NO: 4. Preferably, the first strand of the present dsODN comprises a nucleotide sequence at least 90% identical to SEQ ID NO: 3, and/or the second strand of the present dsODN comprises a nucleotide sequence at least 90% identical to SEQ ID NO: 4. More preferably, the first strand of the present dsODN comprises a nucleotide sequence at least 95% identical to SEQ ID NO: 3, and/or the second strand of the present dsODN comprises a nucleotide sequence at least 95% identical to SEQ ID NO: 4. In one specific example, the first and second strands of the present dsODN respectively comprise the nucleotide sequences of SEQ ID NOs: 3 and 4, i.e., 100% identical to SEQ ID NOs: 3 and 4.

Depending on intended purposes, the present dsODN may have a phosphodiester backbone (i.e., two nucleotides are linked by a phosphodiester bond, in which the phosphate group attached to the 5' carbon of the sugar moiety on one nucleotide forms an ester bond with the free hydroxyl on the 3' carbon of the next nucleotide), a phosphorothioate backbone (i.e., two nucleotides are linked by a phosphorothioate bond, a modified phosphodiester linkage where one of the two non-bridging oxygen is replaced by a sulfur atom), a morpholino backbone (i.e., nucleobases are attached to a backbone of methylenemorpholine rings linked through phosphorodiamidate groups), or a hybrid backbone (e.g., a mixed phosphodiester-phosphorothioate backbone).

According to some embodiments of the present disclosure, the treatment of the present dsODN up-regulates the expression levels of M1 macrophage-associated genes (including IL-12p40, IFN-γ and CCL2), and down-regulates the expression levels of M2 macrophage-associated genes (including IL-10, VEGF-A, TGF-β, PD-L1 and PD-L2) in IL-4- or cancer cell-stimulated macrophages.

According to certain embodiments of the present disclosure, the treatment of the present dsODN enhances the infiltration of CD8 T cells, natural killer cells (NK cells) and B cells into the tumor, and decreases the number of regulatory T cells (Treg cells, also known as suppressor T cells with immunosuppressive properties) and neutrophils in the tumor.

The second aspect of the present disclosure pertains to a composition for treating cancers. According to certain embodiments of the present disclosure, the composition comprises the present dsODN and a pharmaceutically acceptable carrier.

Depending on desired purposes, the pharmaceutically acceptable carrier may be a nanoparticle (NP; e.g., lipid NP, metal NP, ceramic NP, polymeric NP and semiconductor NP), diluent, dispersion medium, buffer, stabilizing agent, or any solutions or substances compatible with pharmaceutical administration.

Generally, the dsODN of this invention is present at a level of about 0.1% to 99% by weight, based on the total weight of the composition. In some embodiments, the dsODN of this invention is present at a level of at least 1% by weight, based on the total weight of the composition. In certain embodiments, the dsODN is present at a level of at least 5% by weight, based on the total weight of the composition. In still other embodiments, the dsODN is present at a level of at least 10% by weight, based on the total weight of the composition. In still yet other embodiments, the dsODN is present at a level of at least 25% by weight, based on the total weight of the composition.

According to some preferred embodiments, the pharmaceutically acceptable carrier is a lipid nanoparticle (LNP; e.g., a liposome) comprising a hydrophilic core and an outer lipid bilayer encapsulating the hydrophilic core. In these embodiments, the present dsODN is present in the hydrophilic core of the LNP.

In certain embodiments, the outer lipid bilayer is formed by a cholesterol and/or one or more phospholipids. Examples of the phospholipid suitable for forming the outer lipid bilayer of the present LNP include, but are not limited to, phosphatidylethanolamine (PE), phosphatidylcholine (PC), phosphatidylserine (PS), distearoylphosphatidylethanolamine (DSPE), dioleoylphosphatidylethanolamine (DOPE), dioleoylphosphatidylcholine (DOPC), distearoylphosphatidylcholine (DSPC), 1,2-dioleoyl-3-trimethylammonium propane (DOTAP), 1,2-distearoyl-3-trimethylammonium propane (DSTAP), 1,2-dimyristoyl glycerol (DMG), 2,3-dioleyloxy-N-[2(sperminecarboxamido)ethyl]N,N-dimethyl-1-propan-aminium (DOSPA), ceramide phosphorylcholine, ceramide phosphorylethanolamine, and ceramide phosphoryllipid. Optionally, the phospholipid is modified with a polyethylene glycol (PEG) so as to prevent aggregation and/or prolong the half-life of the LNP. The term "polyethylene glycol" (PEG) as used herein refers to oligomers and/or polymers of ethylene oxide, and in general refers to those with a molecular mass below 20,000 g/mol (e.g., PEG 400, PEG 2000, and etc). In some preferred embodiments, the outer lipid bilayer of the present LNP is formed by DOSPA and DOPE. According to one embodiment, the ratio of the DOSPA and DOPE in the present LNP is about 3:1 (w/w).

According to some embodiments of the present disclosure, a cholesterol is mixed with a phospholipid (e.g., DSPC) and a PEG-modified phospholipid (e.g., DMG-PEG 2000) in an alcohol solution (e.g., ethanol); the dsODN is then added to the lipid mixture followed by subjecting the mixture to a microfluidic device so as to produce the present composition. Alternatively, the present composition may be produced by any conventional techniques known in the related art.

Optionally, the LNP may have a targeting molecule (e.g., an antibody or an aptamer specific to a tumor antigen) conjugated thereon so as to improve the targeting and therapeutic efficacies of the present composition.

Alternatively, the dsODN of the present disclosure may be formulated into liquid compositions, which are sterile solutions or suspensions that can be administered by parenteral injection, for example, intratumoral, intravenous, intraarterial, intramuscular, subcutaneous or intraperitoneal injection. When the present dsODN is formulated to be administered by parenteral injection, the dsODN would be in the form of a pyrogen-free, parenterally acceptable aqueous solution. The preparation of such parenterally acceptable polypeptide solutions, having due regard to pH, isotonicity, stability, and the like, is within the skill in the art. A preferred composition for parenteral injection should contain, in addition to the present dsODN, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the invention may also contain stabilizers, preservatives, buffers, antioxidants, or other additives known to those of skill in the art. The duration of parenteral therapy using the composition of the invention will vary, depending on the severity of the disease being treated and the condition and potential idiosyncratic response of each individual subject. Ultimately the attending physician will decide on the appropriate duration of parenteral therapy.

Optionally, for the purpose of improving the therapeutic effect on cancers, the present composition may further comprise an anti-cancer agent. According to some embodiments, the pharmaceutically acceptable carrier is a LNP comprising a hydrophilic core and an outer lipid bilayer encapsulating the hydrophilic core, in which the present dsODN and the anti-cancer agent are present in the hydrophilic core of the LNP.

Exemplary anti-cancer agents include, but are not limited to, curcumin, interferon, cytokine (e.g., TNF, IFN-α or IFN-γ), antibody (e.g., trastuzumab, bevacizumab, cetuximab, panitumumab, rituximab or tositumomab), anti-estrogen (e.g., tamoxifen, raloxifene or megestrol), LHRH agonist (e.g., goscrclin or leuprolide), anti-androgen (e.g., flutamide or bicalutamide), photodynamic therapy (e.g., vertoporfin, phthalocyanine, photosensitizer Pc4 or demethoxy-hypocrellin A), nitrogen mustard (e.g., cyclophosphamide, ifosfamide, trofosfamide, chlorambucil, estramustine or melphalan), nitrosourea compound (e.g., carmustine or lomustine), alkylsulphonate (e.g., busulfan or treosulfan), triazene (e.g., dacarbazine or temozolomide), platinum containing compound (e.g., cisplatin, carboplatin or oxaliplatin), vinca alkaloid (e.g., vincristine, vinblastine, vindesine or vinorelbine), taxoid (e.g., paclitaxel or a paclitaxel equivalent as nanoparticle albumin-bound paclitaxel, docosahexaenoic acid bound-paclitaxel (DHA-paclitaxel), polyglutamate bound-paclitaxel (e.g., PG-paclitaxel or paclitaxel poliglumex), the tumor-activated prodrug (TAP) ANG1005 (Angiopep-2 bound to three molecules of paclitaxel), epipodophyllin (e.g., etoposide, etoposide phosphate, teniposide, topotecan, 9-aminocamptothecin, camptoirinotecan, irinotecan, crisnatol or mytomycin C), anti-metabolite, DHFR inhibitor (e.g., methotrexate, dichloromethotrexate, trimetrexate or edatrexate), IMP dehydrogenase inhibitor (e.g., mycophenolic acid, tiazofurin, ribavirin or EICAR), ribonuclotide reductase inhibitor (e.g., hydroxyurea or deferoxamine), uracil analog (e.g., 5-fluorouracil (5-FU), floxuridine, doxifluridine, ratitrexed, tegafur-uracil or capecitabine), cytosine analog (e.g., cytarabine (ara C), cytosine arabinoside or fludarabine), purine analog (e.g., mercaptopurine or thioguanine), vitamin A analog, vitamin D3 analog (e.g., EB 1089, CB 1093 or KH 1060), vitamin K, isoprenylation inhibitor (e.g., lovastatin), dopaminergic neurotoxin (e.g., 1-methyl-4-phenylpyridinium ion), cell cycle inhibitor (e.g., staurosporine), actinomycin (e.g., actinomycin D or dactinomycin), bleomycin (e.g., bleomycin A2, bleomycin B2 or peplomycin), anthracycline (e.g., daunorubicin, doxorubicin (DOX), pegylated liposomal doxorubicin, idarubicin, epirubicin, pirarubicin, zorubicin or mitoxantrone), MDR inhibitor (e.g., verapamil), $Ca^{2+}$-ATPase inhibitor (e.g., thapsigargin), imatinib, thalidomide, lenalidomide, tyrosine kinase inhibitor (e.g., axitinib, bosutinib, cediranib, dasatinib, erlotinib, gefitinib, imatinib, lapatinib, lestaurtinib, neratinib, nilotinib, semaxanib, sunitinib, toceranib, vandetanib, vatalanib, trastuzumab, bevacizumab, rituximab, cetuximab, panitumumab, ranibizumab, nilotinib, sorafenib, everolimus, alemtuzumab, gemtuzumab ozogamicin or temsirolimus), proteasome inhibitor (e.g., bortezomib), mTOR inhibitor (e.g., rapamycin or temsirolimus), everolimus, ridaforolimus, oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Also disclosed herein is a method of treating a cancer in a subject. The method comprises administering to the subject an effective amount of the dsODN or composition in accordance with any embodiments of the present disclosure.

Examples of cancer treatable by the present dsODN or composition include, but are not limited to, gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, and head and neck squamous cell carcinoma.

Depending on desired purposes, the present dsODN or composition may be administered to the subject via any suitable routes, for example, intratumoral, intravenous, intraarterial, intramuscular, subcutaneous or intraperitoneal injection.

According to some embodiments, the subject is a mouse, in which the present dsODN or composition is administered to the subject in the amount of about 1 µg/Kg to 10 mg/Kg body weight per dose; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1,000 µg/Kg body weight per dose; or 2, 3, 4, 5, 6, 7, 8, 9 or 10 mg/Kg body weight per dose.

A skilled artisan could calculate the human equivalent dose (HED) of the present dsODN or composition, based on the doses determined from animal models. Accordingly, the effective HED of the present dsODN or composition is about 0.1 µg/Kg to 1,000 µg/Kg body weight per dose for human; in other words, the effective HED of the present dsODN or composition may be any of, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Preparation of Decoy ODNs

The sense and antisense strands of CYBB decoy ODN were respectively synthesized followed by annealing (heating at 94° C. for 5 minutes and incubating at 25° C. for 3 hours) and purifying with sodium acetate and 100% ethanol. Scrambled decoy ODN serving as a negative control was also produced by similar manner. The nucleotide sequences of the thus-obtained decoy ODNs were summarized in Table 1. The decoy ODNs were dissolved in ddH$_2$O for following study.

TABLE 1

Nucleotide sequences of specified decoy ODNs

| Name | Sequence (5'-end to 3'-end) | SEQ ID NO |
|---|---|---|
| CYBB decoy ODN -sense strand | CTGACTCCCAGGTTCAAGTGATTCTCCT | 3 |
| CYBB decoy ODN -antisense strand | AGGAGAATCACTTGAACCTGGGAGTCAG | 4 |
| scramble decoy ODN -sense strand | CGAAAATTCGTTAAATCACTAGCTTACC | 5 |
| scramble decoy ODN -antisense strand | GGTAAGCTAGTGATTTAACGAATTTTCG | 6 |

920, 930, 940, 950, 960, 970, 980, 990 or 1,000 µg/Kg body weight per dose for human. The dose can be administered in a single aliquot, or alternatively in more than one aliquot. The skilled artisan or clinical practitioner may adjust the dosage or regime in accordance with the physical condition of the patient or the severity of the diseases.

Depending on desired purpose, the present dsODN or composition may be administered to the subject daily, twice per day, or every other day. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer.

The subject treatable by the present method is a mammal, for example, a human, a mouse, a rat, a hamster, a guinea pig, a rabbit, a dog, a cat, a cow, a goat, a sheep, a monkey, and a horse. Preferably, the subject is a human.

As could be appreciated, the present method can be applied to the subject, alone or in combination with additional therapy (e.g., the anti-cancer agents described above) that has some beneficial effects on the prevention or treatment of cancers. Depending on the intended/therapeutic purpose, the present method can be applied to the subject before, during, or after the administration of the additional therapy.

The following Examples are provided to elucidate certain aspects of the present invention and to aid those of skilled in the art in practicing this invention. These Examples are in no way to be considered to limit the scope of the invention in Preparation of Liposome-Clad Decoy ODN The liposome-clad decoy ODN was produced by LIPO-FECTAMINE™ according to the manufacturer's protocol. In brief, the CYBB decoy ODN was added to a master DNA mix by diluting DNA and P3000 reagent in OPTI-MEM™ medium and preparing LIPOFECTAMINE™ 3000 diluted in OPTI-MEM™ medium. The diluted DNA and LIPO-FECTAMINE™ 3000 were mixed at a molar ratio of 1:1, and then incubated for 30 minutes at room temperature to form liposome-clad decoy ODN. The thus-obtained liposome-clad decoy ODN comprised an LNP formed by DOSPA and DOPE (3:1, w/w), and the CYBB decoy ODN encapsulated in the LNP.

Transduction of U937 Cells

U937 cells (a cell line exhibiting monocyte morphology that is used extensively as an in vitro model for human macrophage differentiation) were cultured in complete RPMI1640 media containing 10% fetal bovine serum (FBS). The liposome-clad decoy ODN or CYBB decoy ODN was added to U937 cells, followed by incubating at 37° C. for 24 hours. Then, the U937 cells were treated with IL-4 (20 ng/ml) or co-cultured with PANC-1 cells for 72 hours.

Animal Study

Luciferase-expressing KPC cells (KPC$^{LUC}$, 1×10$^7$ in 50 µL serum-free medium) were orthotopically injected into the pancreas of aged 8-12 weeks male C57BL/6 mice. Two weeks later, the decoy ODN (scrambled decoy ODN or CYBB decoy ODN; 1 µg/Kg) was intravenously administered to the tumor-bearing mice once per week for 3 consecutive weeks. Tumor volumes were monitored weekly by using In vivo imaging system (IVIS).

Isolation and Differentiation of Murine Bone-Marrow Derived Macrophages

Bone marrow cell suspensions were isolated by flushing femurs and tibias of 8-12 weeks old wild-type mice and $Cybb^{-/-}$ mice with complete RPMI1640 media. Aggregates were dislodged by gentle pipetting, and debris was removed by massaging the suspension through a 70 μm nylon web. Cells were washed twice with Hanks' balanced salt solution (HBSS), adjusted to give $10^6$ cells/mL suspension, and seeded in low attachment surface dishes. Cells were supplemented with 20 ng/μL recombinant murine granulocyte-macrophage colony-stimulating factor (rmGM-CSF) and cultured in a humidified incubator at 37° C. and 5% $CO_2$.

Immunohistochemistry (IHC) Analysis

Paraffin-embedded slides were deparaffinized, and antigens were unmasked by autoclaving at 121° C. for 10 minutes in sodium citrate (10 mM; pH 6.0) buffer. For macrophage phenotype identification, the specimens were respectively stained with anti-F4/80, anti-Ym-1, anti-iNOS and anti-nitrotyrosine antibodies, followed by incubating at 4° C. overnight. Then, all slides were incubated with secondary antibodies at room temperature for 30 minutes. The immunoreactivity was observed using chromogen system. The cell nuclei were stained with hematoxylin.

RNA Isolation and Quantitative Polymerase Chain Reaction (PCR)

Total RNA was isolated from cultured cells by TRIZOL™ reagent. The purity and concentration of RNA were determined by spectrophotometer. Then, total RNA from each sample was reverse transcribed into 2 ug cDNA by using reverse transcriptase. The levels of mRNA were determined by quantitative real-time PCR. The reaction conditions were set as follows: initial denaturation at 95° C. for 3 minutes, 40 cycles of denaturation at 95° C. for 3 seconds, and annealing at 60° C. for 20 seconds. The mRNA level was determined by the 2-ΔΔCt method (fold difference) and normalized by software.

Detection of Reactive Oxygen Species (ROS) and Flow Cytometry Analysis

Dichlorodihydrofluorescein diacetate (DCFDA) was used to measure intracellular ROS in the study. The fluorescence-activated cells were analyzed by flow cytometer. The statistics presented were based on 10,000 events gated on the population of interest.

For macrophage phenotype identification, human cell lines ($2\times10^5$ cells) were respectively stained with fluorescence conjugated anti-CD68, anti-CD86 and anti-CD204 antibodies, and murine cells ($2\times10^5$ cells) were respectively stained with fluorescence conjugated anti-F4/80, anti-CD206 and anti-CD11b antibodies. After washed by phosphate buffered saline (PBS), cells were analyzed by flow cytometer.

Statistical Analysis

Data from at least three independent experiments under identical conditions were expressed as the mean±standard error of the mean (SEM). Student's t-test was used to analyze the differences between groups. Statistical analyses were performed using software. Statistical probability (p) was expressed as *$p<0.001$, $p<0.01$, and *$p<0.05$.

Example 1 Orthotopic Pancreatic Tumors in
$Cybb^{-/-}$ Mice 1.1 Tumor Growth and Cell Populations in $Cybb^{-/-}$ Mice It is reported that NOX2 (NADPH oxidase 2, a protein encoded by CYBB gene) plays a role in regulating carcinogenesis and tumor progression. To verify the effect of NOX2 on macrophage polarization and pancreatic tumorigenesis in vivo, luciferase-expressing mouse KPC cells ($KPC^{LUC}$; a cell line derived from pancreatic ductal adenocarcinoma) were orthotopically transplanted into the pancreas of Cybb knockout ($Cybb^{-/-}$) mice, and the tumor growth was monitored using IVIS. Tumor weight and tumor volume were measured after mice were sacrificed at weeks 1, 2, 3, 5 and 7.

According to the IVIS results, the bioluminescence gradually increased in the pancreas in situ of wild-type (WT) mice after inoculation of cancer cells but decreased in that of $Cybb^{-/-}$ mice from week 2 ($P<0.001$) (data not shown). The data further confirmed that the volume and weight of orthotopic pancreatic tumors were significantly lower in $Cybb^{-/-}$ mice than in WT mice ($P<0.001$) (data not shown).

The analytic results of immunohistochemistry (IHC) staining for the total macrophage marker F4/80, the M1 macrophage marker iNOS, and the M2 macrophage marker YM-1 in orthotopic pancreatic tumors from mice demonstrated that there was no difference in $F4/80^+$ cell number between WT and $Cybb^{-/-}$ mice, but more $YM-1^+$ cells and fewer $iNOS^+$ cells were observed in tumors of WT mice as compared to that of $Cybb^{-/-}$ mice (data not shown). The data of western blotting suggested that the expression of iNOS in the tumor of WT mice was lower than that of $Cybb^{-/-}$ mice, and the expression of CD206 (an M2 macrophage marker) in the tumor of WT mice was obviously higher than that of $Cybb^{-/-}$ mice (data not shown). Furthermore, the expression of nitrotyrosine, a metabolic product after reactive oxygen species (ROS) stimulation, was decreased in $Cybb^{-/-}$ mice (data not shown).

The cell populations were further confirmed by flow cytometry. The data indicated that the percentages of $F4/80^+$ $CD206^+$ cells (M2-like macrophages) in the TAM population were reduced in $Cybb^{-/-}$ tumors (10.9%) as compared to that of WT tumors (42%) (data not shown).

In addition to cell populations, tumor-related cytokines were also examined by enzyme-linked immunosorbent assay (ELISA) in this example. According to the analytic results, compared to WT mice, $Cybb^{-/-}$ mice exhibited higher serum levels of Th1 cytokines (IL-12p40 active form and TNF-α) and lower serum levels of Th2 cytokines (IL-4 and IL-10) (data not shown).

Next, whether knockout of Cybb impedes the activation of macrophages from monocytes was examined. Bone marrow cells isolated from the thighbone of $Cybb^{-/-}$ mice could be differentiated into $CD68^-F4/80^+$ bone marrow-derived macrophages (BMDMs) via the stimulation of macrophage colony-stimulating factor (M-CSF), in which no ROS production was observed in $Cybb^{-/-}$ BMDM cells (data not shown). These findings revealed that reduced ROS production in $Cybb^{-/-}$ mice inhibited the formation of M2-like TAMs and consequently suppressed pancreatic tumor growth; however, the reduction of ROS in $Cybb^{-/-}$ mice does not affect the activation of macrophages from monocytes.

The polarization ability of BMDMs was also examined in the study. After co-incubating with KPC tumor cells, there was no difference in the mRNA level of total macrophage marker (F4/80) between WT and $Cybb^{-/-}$ BMDMs (data not shown). The mRNA levels of M1 macrophage markers (Il-12b, and Nos2) increased at 12 hours but decreased at 72 hours, while the mRNA levels of M2 macrophage markers (Il-10 and Ym1) increased with time in wild-type BMDMs (data not shown). By contrast, co-incubation of KPC tumor cells stimulated Cybb$^{-/-}$ BMDMs to express M1 macrophage markers (Il-12b, and Nos2) and exhibited no effect on the expression of M2 macrophage markers (il10 and Ym1) (data not shown). The data suggested that Cybb$^{-/-}$ BMDMs lost their ability to polarize into M2 phenotype.

The treatment of gp91da-tat (a NOX2 inhibitor) and N-acetylcysteine (NAC; a ROS inhibitor) did not affect the expression of M1 marker CD11b, while significantly decreased the expression of M2 marker CD206 at 72 hours post-treatment in wild-type BMDMs (data not shown). On the other hand, the treatment of H$_2$O$_2$ decreased the expression of M1 marker CD11b, while significantly increased the expression levels of M2 marker CD206 in Cybb$^{-/-}$ BMDMs at 72 hours post-treatment (data not shown).

Taken together, the inhibition of CYBB activity would disturb the formation of M2 TAMs, leading to reduced tumor growth.

1.2 Immune Cells in Cybb$^{-/-}$ Mice

For the purpose of evaluating the effect of Cybb gene on the infiltration of immune cells into tumors, KPC cells were orthotopically transplanted into the pancreas of WT and Cybb$^{-/-}$ mice. The tumors were isolated from the WT and Cybb$^{-/-}$ mice (hereinafter, as the "WT tumor" and "Cybb$^{-/-}$ tumor", respectively) and subjected to IHC staining. According to the results, compared to the WT tumor, there were higher levels of CD8$^+$ T cells, Nkp46$^+$ NK cells and CD19$^+$ B cells, and lower levels of Foxp3$^+$ Treg cells present into the Cybb$^{-/-}$ tumor (data not shown). These data suggested that CYBB plays an important role in the immunomodulation of TME.

Example 2 Characterization of the Decoy ODNs 2.1 Effect of the Decoy ODNs on IL-4-Mediated Immunosuppression It is known that IL-4 induces M2 macrophage polarization via activating the transcription factor STAT6, which enhances the transcription of M2 macrophage-associated genes and decreases the transcription of M1 macrophage-associated genes. The present study discovered that CYBB gene plays a critical role in the IL-4/STAT6-mediated M2 macrophage polarization. In this example, the effect of the present CYBB decoy ODN on IL-4-mediated immunosuppression was investigated. To this purpose, two reporter plasmids (i.e., CYBB-luc plasmid and dCYBB-luc plasmid) were respectively transfected into macrophages via electroporation, in which the CYBB-luc plasmid comprised a wild-typd CYBB promoter and a firefly luciferase reporter gene operably linked to the wild-typd CYBB promoter, and the dCYBB-luc plasmid comprised a STAT6 binding sequence-deleted CYBB promoter (i.e., a mutant CYBB promoter having the STAT6 binding sequence deleted) and a firefly luciferase reporter gene operably linked to the STAT6 binding sequence-deleted CYBB promoter. 24 hours later, the transfected macrophages were further transfected with the CYBB decoy ODN or scrambled decoy ODN via electroporation. The cells were incubated in a cultured medium with or without IL-4. To assess transfection efficiency, the macrophages were co-transfected with a pRL-TK vector, which served as an internal control, so as to normalize the results of the firefly luciferase assay.

According to the results, compared to the scrambled decoy ODN, which reduced IL-4-induced luciferase activity, the treatment of the CYBB decoy ODN recovered the IL-4-reduced luciferase activity; on the other hand, no obvious change in luciferase activity was detected in the cells transfected with the dCYBB-luc plasmid (data not shown). The data demonstrated that the treatment of IL-4 inhibited the activity of CYBB promoter, while the treatment of the CYBB decoy ODN significantly reversed the inhibitory effect of IL-4.

The expression of CYBB gene in U937 cells treated with the decoy ODN was also examined. The data indicated that the treatment of the CYBB decoy ODN increased the mRNA level of CYBB in U937 cells after IL-4 treatment or co-culture with PANC-1 cells (data not shown).

2.2 Effect of the Decoy ODNs on Macrophage Polarization

To further determine whether the treatment of the present CYBB decoy ODN would affect macrophage polarization, the CYBB and scrambled decoy ODNs were respectively transfected into macrophages via electroporation, followed by incubating the transfected macrophages in a culture medium containing IL-4 or PANC-1 cancer cells (ATCC number: CRL-1469). After culturing for 24 hours, total RNAs were extracted from the macrophages, and the expression levels of M1 macrophage- and M2 macrophage-associated genes were determined by quantitative polymerase chain reaction (qPCR).

The data demonstrated that the incubation of macrophages with IL-4 or cancer cells induced M2 macrophage polarization. Compared to the control group (i.e., the macrophages treated with the scrambled decoy ODN), the treatment of the CYBB decoy ODN significantly enhanced the expression levels of M1 macrophage-associated genes (including IL-12, IFN-γ and CCL2), and inhibited the expression levels of M2 macrophage-associated genes (including IL-10, VEGF-A, TGF-β, PD-L1 and PD-L2) in IL-4-treated macrophages or cancer cell co-cultured macrophages (data not shown).

The data indicated that the treatment of CYBB decoy ODN was capable of effectively inhibiting the formation of M2 macrophages.

Example 3 Characterization of the Liposome-Clad Decoy ODN

To evaluate the effect of liposome-clad decoy ODN on macrophages, U937-derived macrophages were respectively treated with the liposome-clad decoy ODN (i.e., CYBB decoy encapsulated in liposome-clad) or CYBB decoy ODN (i.e., "free-ODN", serving as a control group), and then incubated in a culture medium containing IL-4 or PANC-1 cancer cells. The data of FIG. 1 indicated that compared to the free-ODN, the treatment of liposome-clad decoy ODN significantly increase the mRNA level of CYBB in U937-derived macrophages after IL-4 treatment (Panel (A) of FIG. 1) or co-culture with PANC-1 cells (Panel (B) of FIG. 1).

Figure 2:
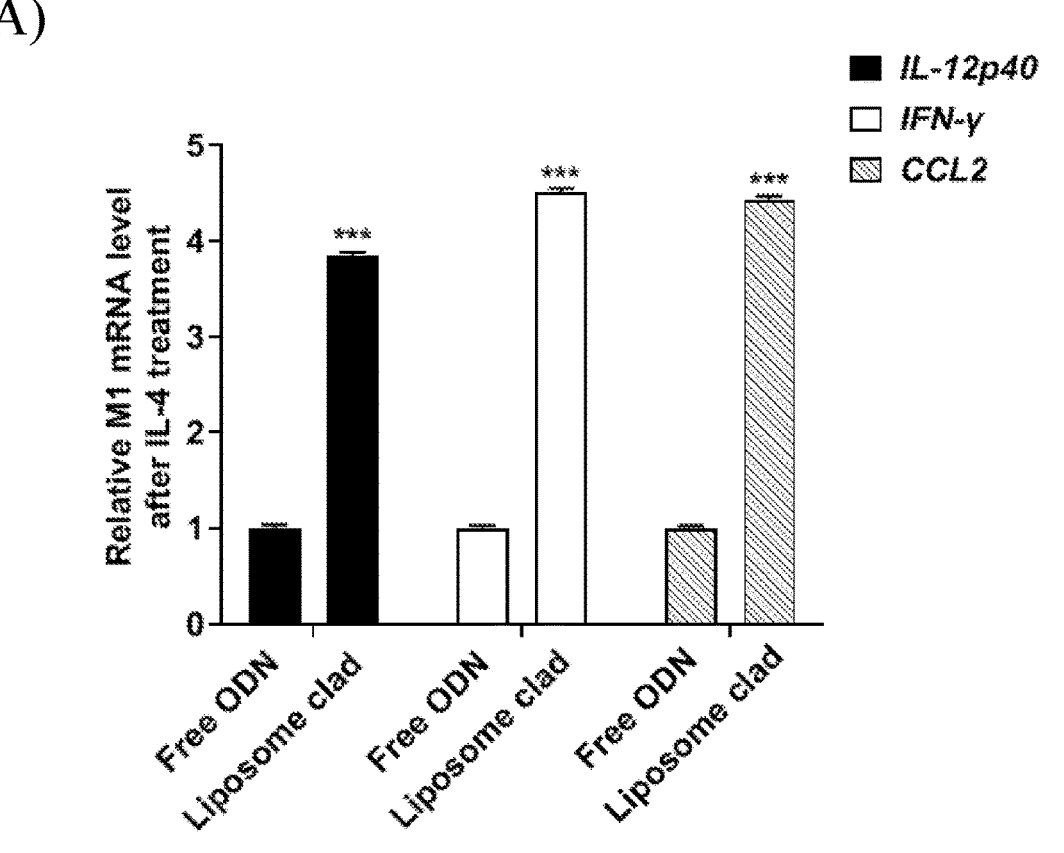
FIG. 2 depicts the effect of liposome-clad decoy ODN on the expression of M1 and M2 cytokines in macrophages according to Example 3 of the present disclosure, in which the U937 cells were treated with CYBB decoy ODN (free-ODN) or liposome-clad decoy ODN (liposome clad), followed by incubating in the medium containing IL-4 or co-incubating with PANC-1 cells. Panel (A): the mRNA levels of M1 cytokines (including IL-12p40, IFN-γ and CCL2) in IL-4-treated U937 cells. Panel (B): the mRNA levels of M1 cytokines (including IL-12p40, IFN-γ and CCL2) in PANC-1 co-incubated U937 cells. Panel (C): the mRNA levels of M2 cytokines (including IL-10, VEGFA and TGFβ) in IL-4-treated U937 cells. Panel (D): the mRNA levels of M2 cytokines (including IL-10, VEGFA and TGFβ) in PANC-1 co-incubated U937 cells. , $p<0.01$; *, $p<0.001$.
Figure 2:
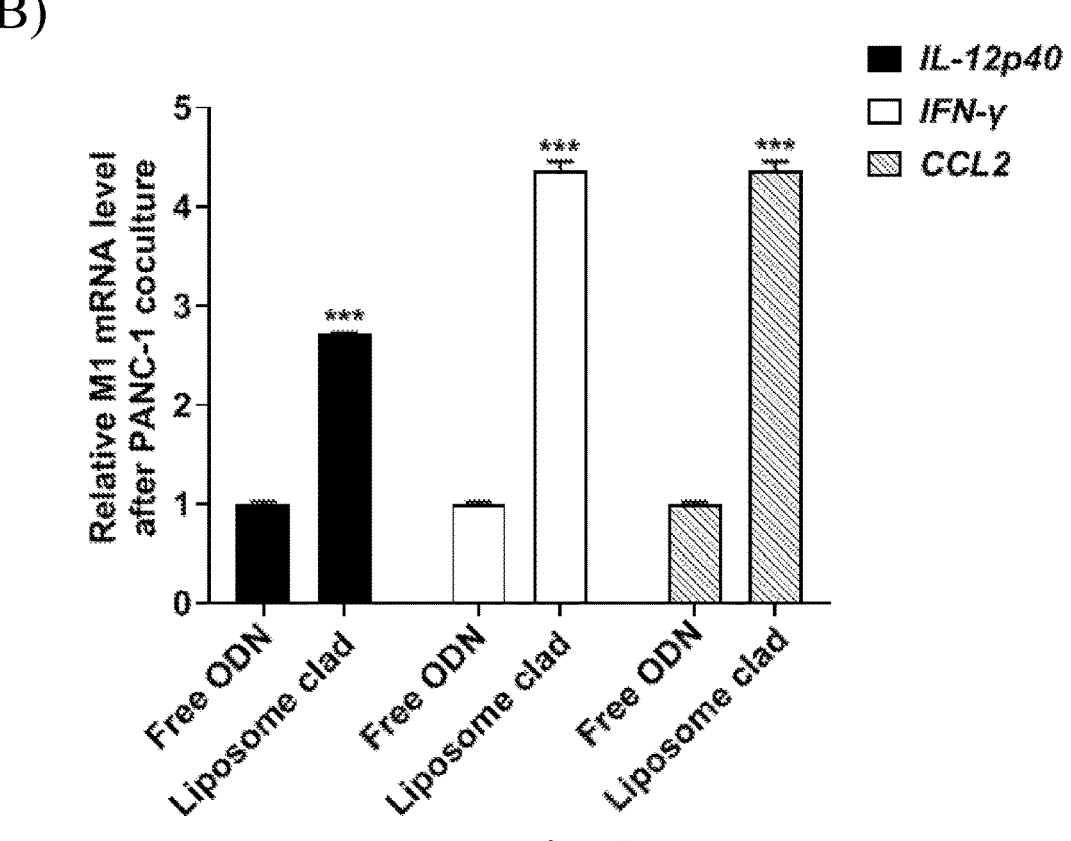
Figure 2:
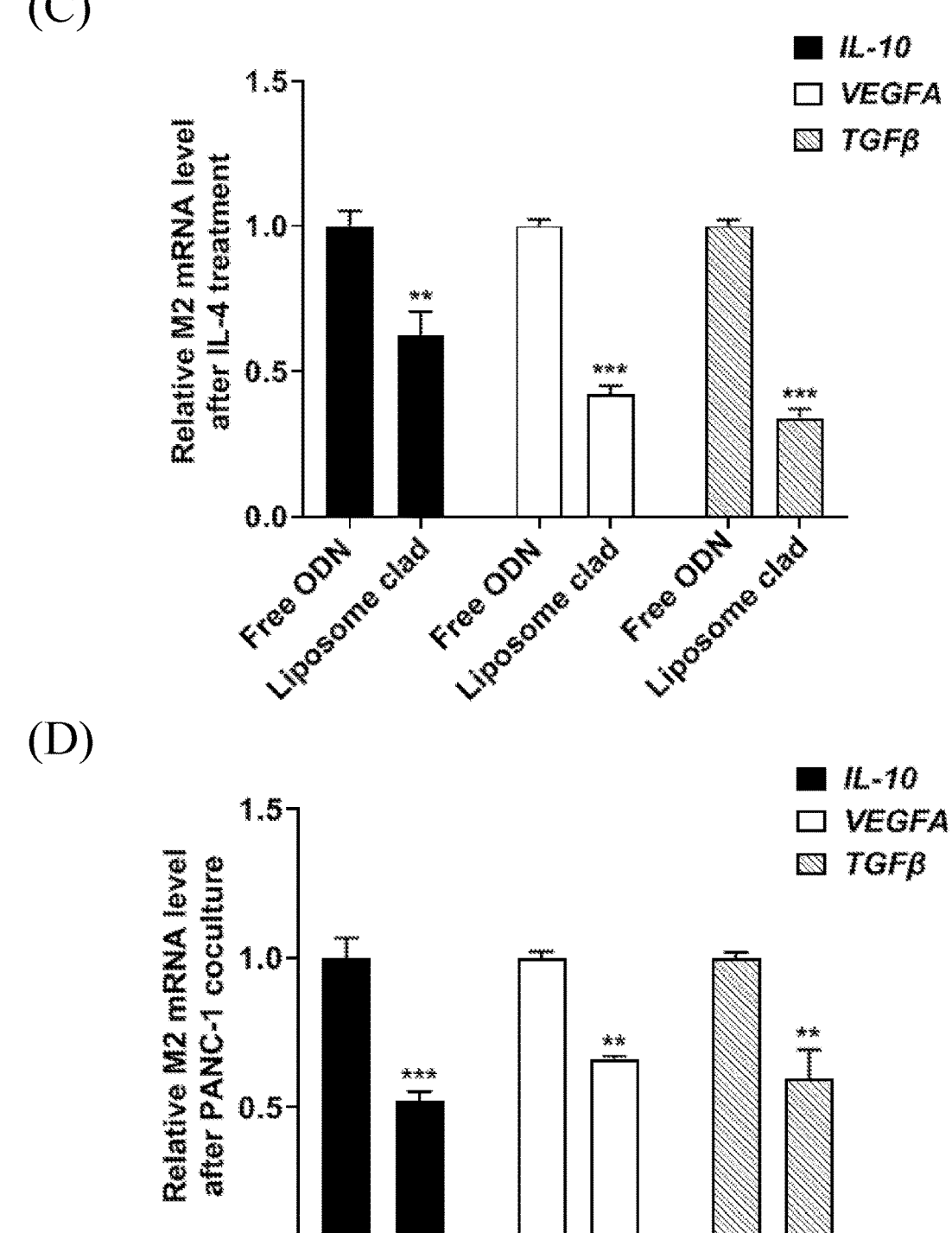

According to the analytic results of ELISA, compared to the free-ODN, the treatment of liposome-clad decoy ODN significantly increased the expression of the M1 cytokines (including IL-12p40, IFN-γ and CCL2), while decreased the expression of the M2 cytokines (including IL-10, VEGFA and TGFβ1) in U937-derived macrophages after IL-4 treatment (Panels (A) and (C) of FIG. 2) or co-culture with PANC-1 cells (Panels (B) and (D) of FIG. 2).

Figure 3:
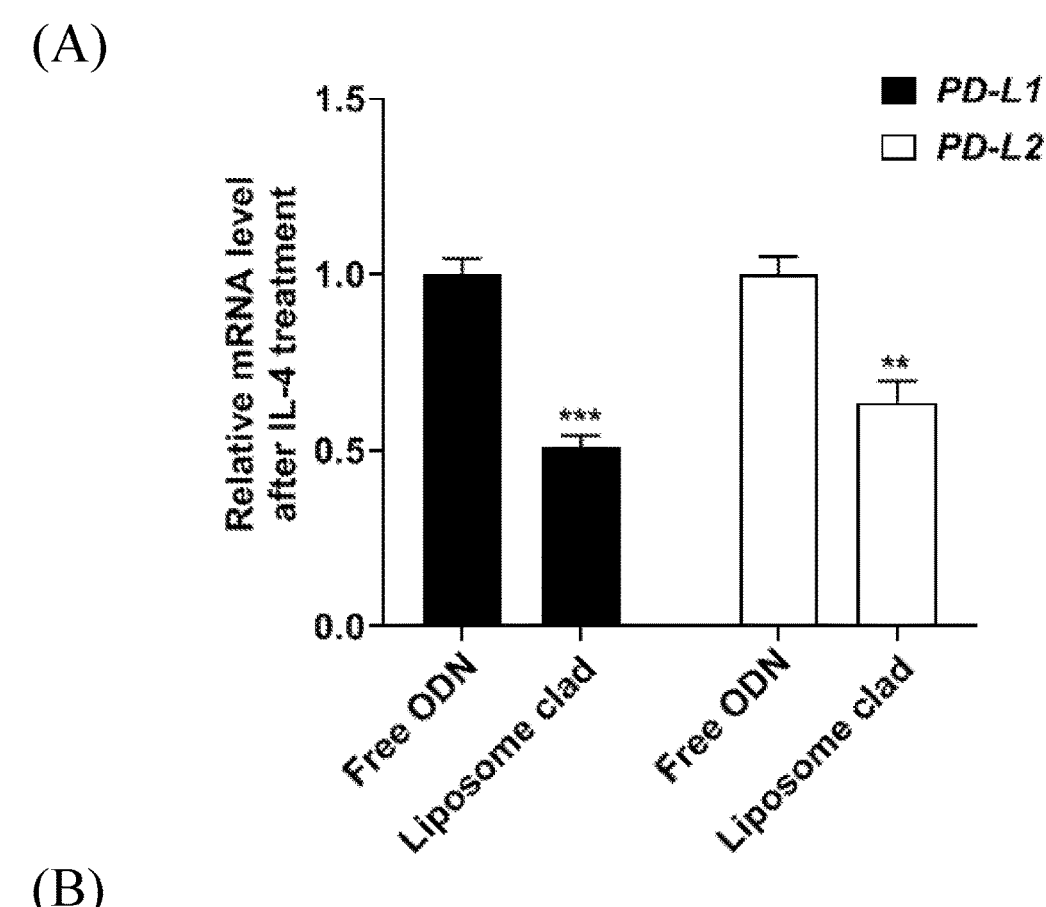
FIG. 3 depicts the effect of liposome-clad decoy ODN on the mRNA levels of PD-L1 and PD-L2 in macrophages according to Example 3 of the present disclosure, in which the U937 cells were treated with CYBB decoy ODN (free-ODN) or liposome-clad decoy ODN (liposome clad), followed by incubating in the medium containing IL-4 (Panel (A)) or co-incubating with PANC-1 cells (Panel (B)). , $p<0.01$; *, $p<0.001$.
Figure 3:
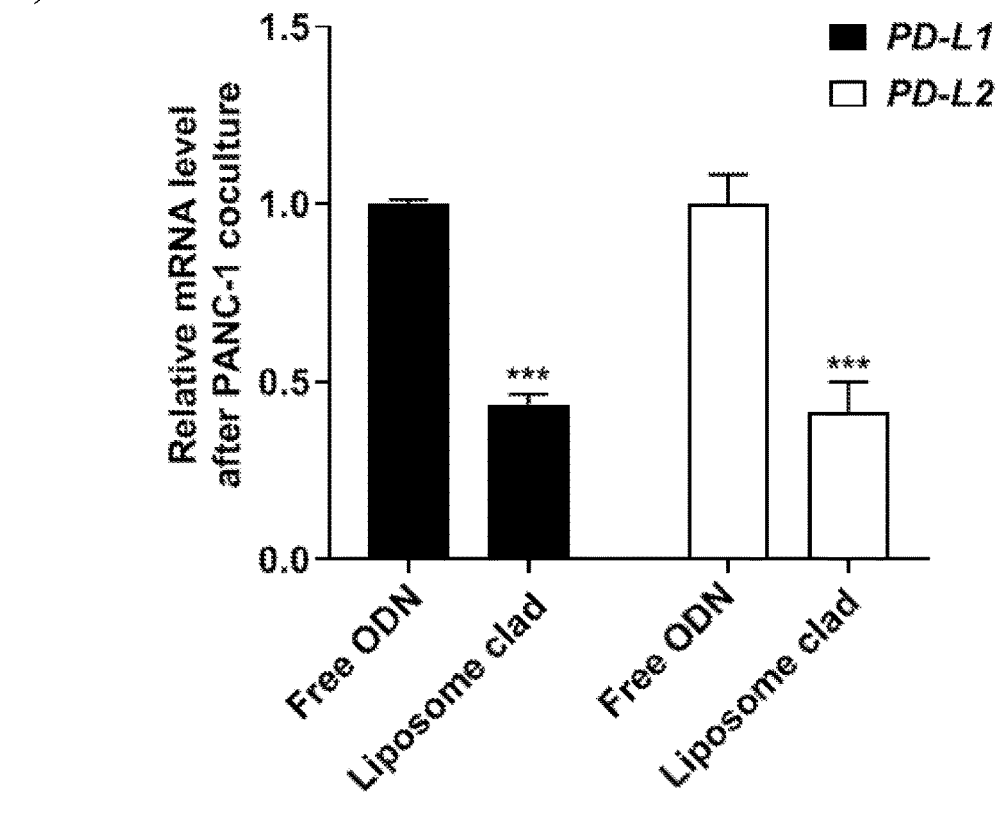

The results of qPCR further confirmed that the treatment of liposome-clad decoy ODN decreased the mRNA levels of PD-L1 and PD-L2 in U937-derived macrophages treated with IL-4 (Panel (A) of FIG. 3) or co-cultured with PANC-1 cells (Panel (B) of FIG. 3).

These results suggested that liposome-clad decoy ODN exhibited higher efficacy in inhibiting M2 macrophage formation as compared to that of free-ODN, and thus may serve as a candidate for the development of medicament for treating cancers or cancer-related diseases.

Example 4 Anti-Tumor Effect in Animal Model

The effects of the present CYBB decoy ODN on macrophage polarization and tumor growth in mice were examined in this example. As described in Materials and Methods, the KPC$^{LUC}$ cells were orthotopically transplanted into the pancreas of WT mice, followed by the treatment of scrambled ODN or CYBB decoy ODN weekly for 3 consecutive weeks.

Figure 4:
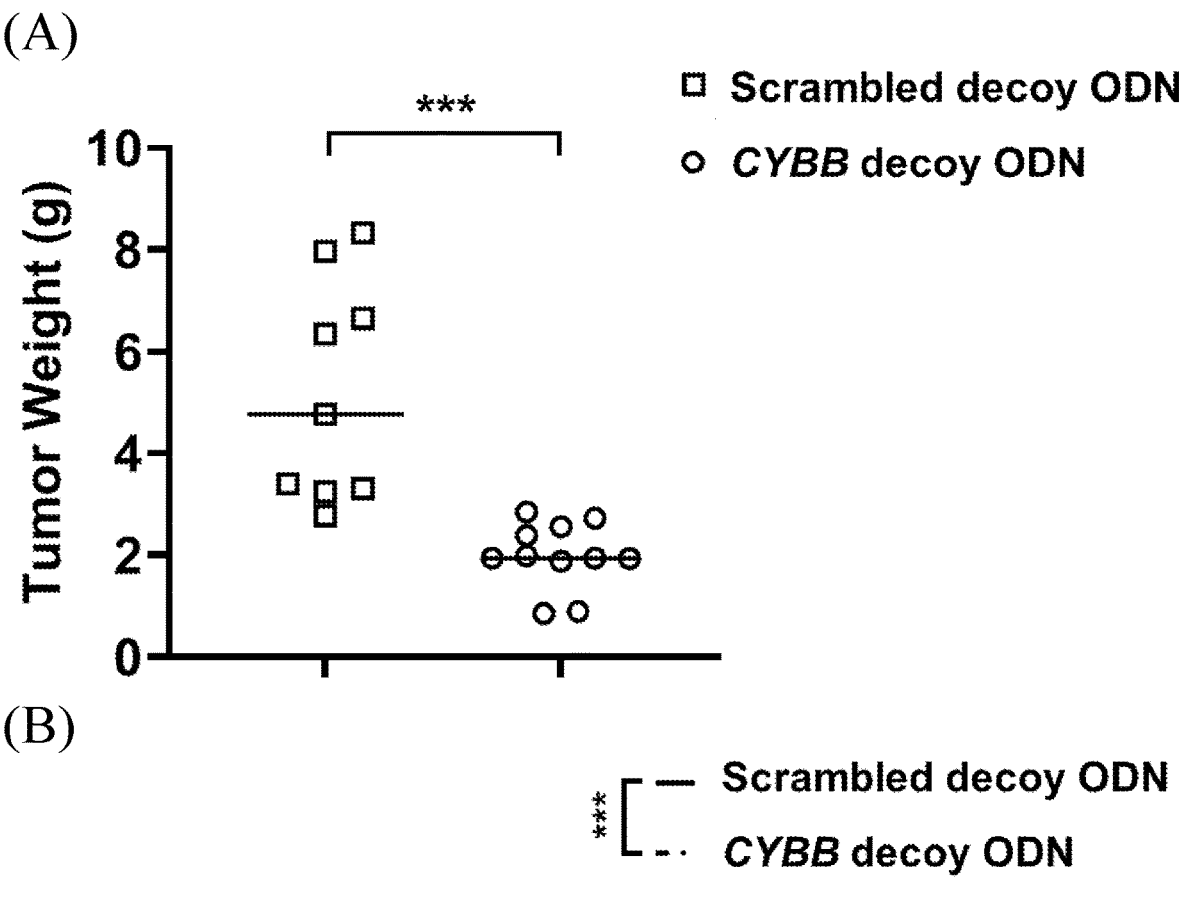
FIG. 4 depicts the effect of CYBB decoy ODN on inhibiting tumor growth (Panel (A)) and prolonging survival time of mice (Panel (B)) according to Example 4 of the present disclosure; N=11 for each group. ***, $p<0.001$.
Figure 4:
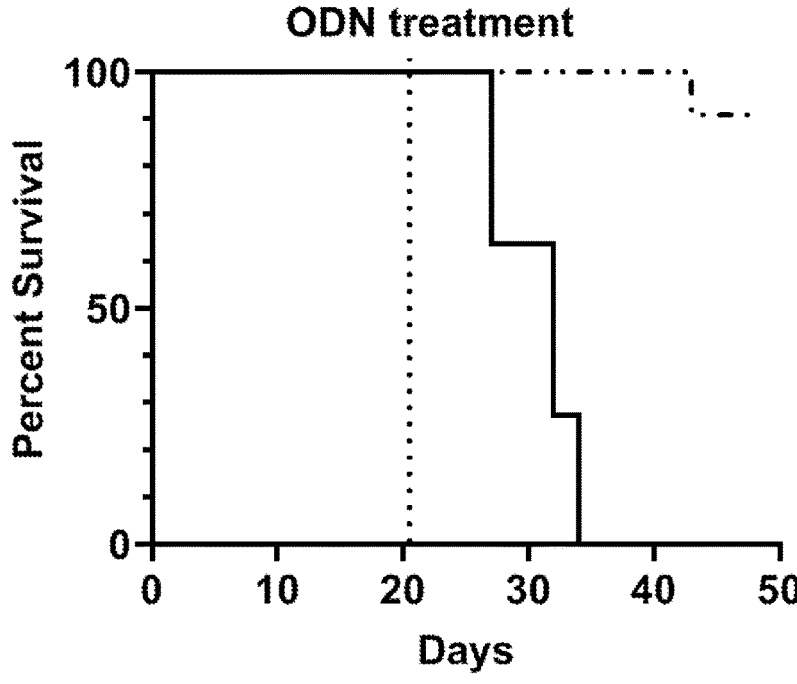

The data of FIG. 4 indicated that the treatment of CYBB decoy ODN significantly inhibited tumor growth in mice (p=0.0003; Panel (A) of FIG. 4), and prolonged the survival time of the tumor-bearing mice (Panel (B) of FIG. 4) as compared to the scrambled ODN treatment. Compared to the scrambled ODN group, there were significantly more iNOS$^+$ cells, and less CD206$^+$, YM-1$^+$ and CD163$^+$ cells present in the tumor of CYBB decoy ODN-treated mice (data not shown). Further, the treatment of CYBB decoy ODN increased the expression levels of caspase 3, cleaved caspase 3 and poly(ADP-ribose) polymerase (PARP), and decreased the expression levels of BCL-XL (an anti-apoptosis marker) and ki67 (a cell proliferation marker) (data not shown), suggesting that the CYBB decoy ODN inhibited tumor growth via promoting cell apoptosis and suppressing cell proliferation.

According to the complete blood count (CBC) test, the treatment of CYBB decoy ODN decreased the percentage of neutrophils, and increased the percentage of lymphocytes as compared to the scrambled decoy ODN treatment (data not shown). The IHC results indicated that compared to the scrambled decoy ODN treatment, there were higher levels of CD3$^+$ lymphocytes, CD8$^+$ T cells, CD56$^+$ NK cells and CD19$^+$ B cells, and lower levels of Foxp3$^+$ Treg cells and Ly6G$^+$ neutrophils present in the tumor of mice receiving CYBB decoy ODN treatment (data not shown).

The liver function test (the serum level of glutamic oxaloacetic transaminase (GOT), glutamic pyruvic transaminase (GPT), albumin (ALB), and total protein (TP)) and renal function test (the serum level of blood urea nitrogen (BUN), uric acid (UA), creatinine (CRE), and lactate dehydrogenase (LDH)) were performed to examine whether the administration of CYBB decoy ODN would affect the liver and renal functions. According to the results, none of the hepatic and renal factors changed after ODN treatment (data not shown), indicating that the decoy ODN did not exhibit hepatotoxicity and nephrotoxicity in mice. These results suggested that the CYBB decoy ODNs was able to treat cancers in a safe and efficient manner.

In conclusion, the present disclosure provides a novel decoy ODN, which is capable of suppressing M2 macrophage polarization via upregulating M1-associated gene expression and downregulating M2-associated gene expression. Based on the inhibitory effect on M2 macrophages, the present CYBB decoy ODN may serve as a potential candidate for the development of a medicament for cancer treatment.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

20

What is claimed is:

1. A composition comprising, a double-stranded oligodeoxynucleotide (dsODN) that inhibits binding of signal transducer and activator of transcription 6 (STAT6) and histone deacetylase 2 (HDAC2) to cytochrome b-245 beta chain (CYBB) promotor, the dsODN comprises a first strand having a nucleotide sequence 100% identical to SEQ ID NO:3, and a second strand complementary to the first strand; and a lipid nanoparticle having a hydrophilic core and an outer lipid bilayer;

wherein, the dsODN is encapsulated within the hydrophilic core of the lipid nanoparticle.

2. A method of treating a cancer in a subject, comprising administering to the subject an effective amount of the composition of claim 1.

3. The method of claim 2, wherein the cancer is gastric cancer, lung cancer, bladder cancer, breast cancer, pancreatic cancer, renal cancer, colorectal cancer, cervical cancer, ovarian cancer, brain tumor, prostate cancer, hepatocellular carcinoma, melanoma, esophageal carcinoma, multiple myeloma, or head and neck squamous cell carcinoma.

4. The method of claim 2, wherein the subject is a human.

* * * * *

SEQUENCE LISTING

```
Sequence total quantity: 6
SEQ ID NO: 1              moltype = DNA   length = 10
FEATURE                   Location/Qualifiers
source                    1..10
                          mol_type = other DNA
                          organism = synthetic construct
SEQUENCE: 1
ttcaagtgat                                                        10

SEQ ID NO: 2              moltype = DNA   length = 10
FEATURE                   Location/Qualifiers
source                    1..10
                          mol_type = other DNA
                          organism = synthetic construct
SEQUENCE: 2
atcacttgaa                                                        10

SEQ ID NO: 3              moltype = DNA   length = 28
FEATURE                   Location/Qualifiers
source                    1..28
                          mol_type = other DNA
                          organism = synthetic construct
SEQUENCE: 3
ctgactccca ggttcaagtg attctcct                                    28

SEQ ID NO: 4              moltype = DNA   length = 28
FEATURE                   Location/Qualifiers
source                    1..28
```

-continued

```
                        mol_type = other DNA
                        organism = synthetic construct
SEQUENCE: 4
aggagaatca cttgaacctg ggagtcag                                        28

SEQ ID NO: 5           moltype = DNA  length = 28
FEATURE                Location/Qualifiers
source                 1..28
                        mol_type = other DNA
                        organism = synthetic construct
SEQUENCE: 5
cgaaaattcg ttaaatcact agcttacc                                       28

SEQ ID NO: 6           moltype = DNA  length = 28
FEATURE                Location/Qualifiers
source                 1..28
                        mol_type = other DNA
                        organism = synthetic construct
SEQUENCE: 6
ggtaagctag tgatttaacg aattttcg                                       28
```